United States Patent [19]
Datta et al.

[11] Patent Number: 5,871,010
[45] Date of Patent: Feb. 16, 1999

[54] INHALER APPARATUS WITH MODIFIED SURFACES FOR ENHANCED RELEASE OF DRY POWDERS

[75] Inventors: Pabitra Datta, Cranbury; Howard Christopher Rivenburg, Princeton; Nitin Desai, Princeton Jct., all of N.J.

[73] Assignee: Sarnoff Corporation, Princeton, N.J.

[21] Appl. No.: 661,213

[22] Filed: Jun. 10, 1996

[51] Int. Cl.[6] ................................................. A61M 15/00
[52] U.S. Cl. ................................. 128/203.15; 128/203.12
[58] Field of Search ........................ 128/203.15, 203.12, 128/203.19, 203.21, 203.23; 156/655.1; 264/482; 430/108

[56] References Cited

U.S. PATENT DOCUMENTS

| | | | |
|---|---|---|---|
| 2,603,216 | 7/1952 | July | 128/203.15 |
| 2,604,094 | 6/1952 | Miller et al. | 128/203.15 |
| 3,831,606 | 8/1974 | Damani | 128/266 |
| 3,971,377 | 7/1976 | Damani | 128/266 |
| 4,047,525 | 9/1977 | Kulessa et al. | 128/208 |
| 4,069,086 | 1/1978 | Reif | 156/378 |
| 4,072,129 | 2/1978 | Bright et al. | 118/629 |
| 4,105,027 | 8/1978 | Lundquist | 128/203.15 |
| 4,160,257 | 7/1979 | Carrish | 346/159 |
| 4,197,289 | 4/1980 | Sturzenegger et al. | 424/21 |
| 4,252,848 | 2/1981 | Datta et al. | 428/64 |
| 4,332,789 | 6/1982 | Mlodozeniec | 424/27 |
| 4,353,365 | 10/1982 | Hallworth et al. | 128/203.15 |
| 4,570,630 | 2/1986 | Elliott et al. | 128/203.15 |
| 4,627,432 | 12/1986 | Newell et al. | 128/203.15 |
| 4,664,107 | 5/1987 | Wass | 128/200.23 |
| 4,685,620 | 8/1987 | Law et al. | 239/3 |
| 4,778,054 | 10/1988 | Newell et al. | 206/531 |
| 4,795,644 | 1/1989 | Zentner | 424/468 |
| 4,811,731 | 3/1989 | Newell et al. | 128/203.15 |
| 4,889,114 | 12/1989 | Kladders | 128/203.15 |
| 4,917,978 | 4/1990 | Ritt et al. | 430/23 |
| 4,921,727 | 5/1990 | Datta et al. | 427/57 |

(List continued on next page.)

FOREIGN PATENT DOCUMENTS

| | | |
|---|---|---|
| 0 129 985 A1 | 1/1985 | European Pat. Off. . |
| 0642992A2 | 8/1994 | European Pat. Off. . |
| 2 064 334 | 6/1981 | United Kingdom . |
| 2 242 134 | 9/1991 | United Kingdom . |
| 2 274 273 | 7/1994 | United Kingdom . |
| WO 93/09832 | 5/1993 | WIPO . |
| WO 93/24166 | 9/1993 | WIPO . |
| WO 94/06497 | 3/1994 | WIPO . |
| WO 94/08552 | 4/1994 | WIPO . |
| WO 94/13271 | 6/1994 | WIPO . |
| WO 94/23772 | 10/1994 | WIPO . |
| WO 95/00127 | 1/1995 | WIPO . |

OTHER PUBLICATIONS

Donald A. Seanor, Triboelectrification of Polymers in K.C. Frisch and A. Patsis, Electrical Properties of Polymers (Technomic Pubcations, Westport, CT) p.p. 37–58.

(List continued on next page.)

*Primary Examiner*—John G. Weiss
*Assistant Examiner*—V. Srivastava
*Attorney, Agent, or Firm*—William J. Burke

[57] ABSTRACT

In one aspect, the present invention provides an inhaler apparatus comprising interior surfaces having contact with a medicament for inhalation, the interior surfaces including an interior surface of a mouthpiece and a substrate with medicament deposited thereon at least one of such interior surfaces comprising indentations or raised areas therein, the raised areas having valleys therebetween. In certain preferred embodiments, the interior surface is a surface on a substrate having medicament deposited thereon, and in other preferred embodiments, the interior surface is an interior surface of the mouthpiece of the inhaler. In addition to providing surface topology for minimizing the area of contact between the medicament and the surfaces of the inhaler, the surfaces are preferably made of a material having a low surface energy, and more preferably, also having, when uncharged, no substantial van der Waals or electrostatic interaction with the medicament. Furthermore, the material is preferably substantially chemically unreactive with the medicament.

31 Claims, 8 Drawing Sheets

U.S. PATENT DOCUMENTS

| | | | |
|---|---|---|---|
| 4,921,767 | 5/1990 | Datta et al. | 430/23 |
| 4,971,257 | 11/1990 | Birge | 239/708 |
| 5,028,501 | 7/1991 | Ritt et al. | 430/23 |
| 5,031,610 | 7/1991 | Armstrong et al. | 128/200.23 |
| 5,035,237 | 7/1991 | Newell et al. | 128/203.15 |
| 5,115,803 | 5/1992 | Sioutas | 128/200.23 |
| 5,161,524 | 11/1992 | Evans | 128/203.15 |
| 5,176,132 | 1/1993 | Drought et al. | 128/203.15 |
| 5,239,993 | 8/1993 | Evans | 128/203.15 |
| 5,243,970 | 9/1993 | Ambrosio et al. | 128/203.15 |
| 5,263,475 | 11/1993 | Altermatt et al. | 128/203.15 |
| 5,278,588 | 1/1994 | Kubelik | 346/159 |
| 5,301,666 | 4/1994 | Lerk et al. | 128/203.15 |
| 5,327,883 | 7/1994 | Williams et al. | 128/203.12 |
| 5,415,162 | 5/1995 | Casper et al. | 128/203.12 |
| 5,462,701 | 10/1995 | Hagemeyer et al. | 264/482 |
| 5,507,281 | 4/1996 | Kuhnel et al. | 128/203.15 |
| 5,512,131 | 4/1996 | Kumar et al. | 156/655.1 |
| 5,619,984 | 4/1997 | Hodson et al. | 128/203.15 |
| 5,652,079 | 7/1997 | Mochizuki et al. | 430/108 |

OTHER PUBLICATIONS

Toshiya Watanabe et al., Electrostatic Force and Absorption Current of Alumina Electrostatic Chuck, Jpn. J. Appl. Phys. vol. 31, pp. 2145–2150 (1992).

Larry D. Harsough, Electrostatic Wafer Holding, Solid State Technology, pp. 87–90 (Jan. 1993).

John Field, Electrostatic Wafer Clamping for Next–Generation Manufacturing, Solid State Technology, pp. 91–98 (Sep. 1994).

J. –F. Daviet et al., Electrostatic Clamping Applied to Semiconductor Plasma Processing, I. Theoretical Modeling, J. Electrochem. Soc., vol. 140, No. 11, pp. 3245–3256 (Nov. 1993).

J. –F. Daviet et al., Electrostatic Clamping Applied to Semiconductor Plasma Processing, II. Experimental Results, J. Electrochem. Soc., vol. 140, No. 11, pp. 3256–3261 (Nov. 1993).

Peter Singer, Electrostatic Chucks in Wafer Processing, Semiconductor International, pp. 57–64 (Apr. 1995).

T. Watanabe et al., Electrostatic Charge Distribution in The Dielectric Layer of Alumina Electrostatic Chuck, Journal of Materials Science, vol. 29, pp. 3510–3616 (1994).

Mamoru Nakasuji et al., Low Voltage and High Speed Operating Electrostatic Wafer Chuck Using Sputtered Tantalum Oxide Membrane, J. Vac. Sci. Technol. A 12(5) pp. 2834–2839 (Sep./Oct. 1994).

INHALER APPARATUS WITH MODIFIED SURFACES FOR ENHANCED RELEASE OF DRY POWDERS

RELATED CO-PENDING U.S. PATENT APPLICATIONS

Related co-pending U.S. patent applications, Ser. Nos. 08/661,212 ("Inhaler Apparatus with an Electronic Means for Enhanced Release of Dry Powders," filed simultaneously herewith), 08/630,049 ("Acoustic Dispenser," filed Apr. 9, 1996, and its continuation-in-part filed simultaneously herewith), 08/630,050 ("Electrostatic Chucks," filed Apr. 9, 1996) and its continuation-in-part, filed simultaneously herewith, 08/630,012 ("Chucks and Methods for Positioning Multiple Objects on a Substrate," filed Apr. 9, 1996), 08/471, 889 ("Methods and Apparatus for Electronically Depositing a Medicament Powder Upon Predefined Regions of a Substrate," filed Jun. 6, 1995, and continuation-in-part thereof filed Jun. 6, 1996), 08/467,647 ("Apparatus for Electrostatically Depositing and Retaining Materials Upon a Substrate," filed Jun. 6, 1995) and 08/506,703 ("Inhaler Apparatus Using a Tribo-Electric Charging Technique," filed Jul. 25, 1995) describe, inter alia, the electrostatic deposition of objects, such as particles of powder, on a substrate, such as an inhaler substrate The foregoing patent applications are hereby incorporated herein by reference, in their entirety.

In one aspect, the present invention provides an inhaler apparatus comprising interior surfaces having contact with a medicament for inhalation, the interior surfaces including the interior of the mouthpiece and the substrate with medicament deposited thereon. According to the invention, at least one of such interior surfaces have indentations or raised areas therein, the raised areas having valleys between them. These surface modifications provide a mechanism for minimizing the area of contact between the medicament and the surfaces of the inhaler, thereby promoting release of the medicament from the inhaler.

Numerous approaches have been taken in the design and manufacture of dry powder inhalers. For example, WO 93/09832 discloses an inhalation device having an elongate carrier of medicament powder, the medicament powder being released after impact from a hammer, the inhalation device having a convoluted channel to deagglomerate the medicament powder.

The disadvantages of the inhalers of the prior art include, for example, the inability of a patient suffering from a respiratory disorder, such as asthma, to inhale with sufficient force to receive an entire dosage. For example, a patient may only be able to generate an air flow rate of about 15 liters per minute. In most dry powder inhalers, the patient's inhalation supplies the energy required to dispense the medicament from the inhaler. The air flow rate generated by the patient's lungs significantly affects the amount of medicament that ultimately exits the inhaler and reaches the lungs.

Another disadvantage of the inhalers of the prior art includes the inability to accurately determine the amount of medicament dispensed, since the inhaler may dispense a greater or lesser amount of medicament, depending upon the patient's air flow rate, for example.

A further disadvantage of the inhalers of the prior art is a problem of agglomeration of the medicament powder. Agglomerated particles generally impact the mouth and throat rather than remaining in the air flow for deposition on the lungs. One of the approaches to remedying this problem has been the provision of tortuous channels in the inhalers of the prior art to promote deagglomeration. This approach suffers from drawbacks, however, such as the deposition of the medicament along the channels, thereby leading to inaccurate dosage dispensing.

Another disadvantage encountered in the inhalers of the prior art is unintended dislodging, in which the medicament is discharged, for example, upon dropping the inhaler.

For the foregoing reasons, there is a need for a dry powder inhaler capable of delivering an accurate unit dosage of medicament at a low flow rate, such as 15 liters per minute, yet which substantially retains the medicament upon impact, such as dropping the inhaler.

SUMMARY OF THE INVENTION

The present invention is directed, in part, to an inhaler apparatus comprising interior surfaces having contact with a medicament for inhalation, the interior surfaces including an interior surface of a mouthpiece and a substrate with medicament deposited thereon, at least one of such interior surfaces comprising indentations or raised areas therein, the raised areas having valleys therebetween. In certain preferred embodiments, the interior surface is a surface on a substrate having medicament deposited thereon, and in other preferred embodiments, the interior surface is an interior surface of the mouthpiece of the inhaler. Preferably, both the surface of the substrate and the mouthpiece and any other surfaces having contact with the medicament have indentations or raised areas therein, or any other surface structure for decreasing the area of contact between the selected medicament and the surface.

In preferred embodiments, the width of the indentations or valleys have a diameter that is about 5% to about 20% smaller and more preferably, about 10% to about 20% smaller than a minimum selected particle size to be administered by the inhaler. In certain preferred embodiments, the width of the indentations or valleys have a diameter of about one micron to about 2.5 microns. Preferably, the depth of the indentations or valleys is also smaller than a minimum selected particle size to be administered by the inhaler, and most preferably, the depth is about 5% to about 50% smaller, and more preferably, about 5% to about 20% smaller than a minimum selected particle size to be administered by the inhaler.

In preferred embodiments, the indentations or valleys are substantially regularly spaced throughout the area of the substrate having medicament thereon or throughout the mouthpiece of the inhaler. In certain preferred embodiments, the indentations are substantially linear.

The substrate having the medicament deposited thereon can be of any selected shape, including, in preferred embodiments, a disk or a tape. Preferably, the substrate comprises multiple dosage units of medicament. In preferred embodiments, the medicament is sealed onto the substrate.

In addition to providing surface topology for minimizing the area of contact between the medicament and the surfaces of the inhaler, the surfaces are preferably made of a material having a low surface energy, and more preferably, also having, when uncharged, no substantial van der Waals or electrostatic interaction with the medicament. Furthermore, the material is preferably substantially chemically unreactive with the medicament. Examples of materials that can be used for such surfaces include perfluorinated polymers such as polytetrafluoroethylene ("TEFLON"), silicone, silicon alumina ceramic, polymeric photoconductor, polycarbonate, polyimide, polypropylene and polyethylene. In some embodiments, the surface has reacted with a silane, such as fluorosilane or aminosilane, to form a film having a low surface energy. Alternatively, for example, the surface can be treated to apply a perfluorinated polymer film.

Other preferred aspects of the invention include an inhaler apparatus comprising a mouthpiece, the mouthpiece having a wall with an exterior and an interior surface, the mouthpiece further comprising multiple air inlets extending from the exterior to the interior, the inlets each being in communication with a channel, each channel extending from the interior to the exterior of the mouthpiece. Preferably, each channel is positioned at an angle of about 20 to about 70 degrees, and more preferably, about 45 degrees from the wall of the mouthpiece. Preferably, the channels are substantially cylindrical in shape. In certain preferred embodiments, the channels are preferably less than about 5 mm in diameter, such as about 0.1 to about 5 mm in diameter or less than about 0.1 mm in diameter.

Preferably, the interior surface of the mouthpiece further comprises indentations or raised areas therein, the raised areas having valleys therebetween, and the indentations or valleys are preferably substantially parallel to the direction of air flow in the mouthpiece during inhalation. In preferred embodiments, the width of the indentations or valleys is about 5% to about 20% smaller, and more preferably, about 10% to about 20% smaller than the minimum particle size to be administered by the inhaler.

In certain preferred embodiments, the mouthpiece further comprises a shuttering mechanism for selectively closing at least one of the air inlets, such shuttering action preferably being capable of actuation by the patient.

In another aspect, the present invention provides a method of manufacturing an inhaler apparatus, comprising:
(a) providing a substrate having a surface for deposition of medicament, the substrate having indentations or raised areas therein, the raised areas having valleys therebetween;

(b) depositing medicament on the substrate; and (c) incorporating the substrate into a housing.

Preferably, the deposition Is performed electrostatically.
Preferably, the medicament deposited on the substrate has a particle size of about one to about fifteen microns. In preferred embodiments, the methods of the invention include sealing the substrate having medicament deposited thereon.

FIGS. 2A–E are micrographs of release of a powder from a polypropylene substrate with indentations therein, in the form of grooves. The magnification shown in FIGS. 2A–E is 42×. FIG. 2A shows the powder before release; FIG. 2B shows the powder remaining after being subjected to an air flow of 15 liters per minute; FIG. 2C shows the powder remaining after being subjected to an air flow of 30 liters per minute; FIG. 2D shows the powder remaining after being subjected to an air flow of 45 liters per minute; and FIG. 2E shows the powder remaining after being subjected to an air flow of 57 liters per minute.

FIG. 2F is a graphical representation of data obtained for the release of powder from the substrate shown in FIGS. 2A–E at increasing flow rates.

FIGS. 3A–C are photomicrographs of an inhaler substrate. FIG. 3A is a photomicrograph of a polypropylene substrate with indentations therein, in the form of grooves; FIG. 3B is a micrograph of the same substrate with powder deposited thereon, and FIG. 3C is a micrograph of the same substrate after release of the powder.

FIGS. 4A–C are photomicrographs of an inhaler substrate made of silicon with grooved indentations in the surface as the substrate. FIG. 4A is a photomicrograph of the substrate; FIG. 4B is a micrograph of the same substrate with powder deposited thereon, and FIG. 4C is a micrograph of the same substrate after release of the powder.

FIGS. 5A–C show a higher magnification of the photomicrographs of FIGS. 4A–C.

FIGS. 6A–C show a higher magnification of the photomicrographs of FIGS. 5A–C.

FIG. 7 is a photograph of an embodiment of a mouthpiece of an inhaler of the invention, the arrow pointing to the air inlets of the mouthpiece.

FIGS. 8A and 8B are cross-sectional views of one embodiment of the inhaler apparatus of the invention. FIG. 8A shows the inhaler without an electronic assisting means, and FIG. 8B shows the inhaler with an electronic assisting means.

FIG. 9 is a photograph of a set-up used to test release of the powder from the substrate of an inhaler.

FIG. 10 is a graphical representation of the amount of medicament powder released from a planar substrate as compared to a substrate with grooved indentations therein.

DETAILED DESCRIPTION OF THE INVENTION

After depositing a powder onto a substrate of an inhaler, the powder must be accurately released upon inhalation by a patient. One of the obstacles to overcome is the adherence of the powder particles to the substrate. One of the forces holding the particles onto the substrate is a van der Waals force. Another one of the holding forces is the electrostatic force. A third holding force is a charge image force, generated by the charge of the powder particle in the local area of the substrate upon which it is adhered. These forces vary in magnitude depending upon, for example, the conductivity of the substrate. The van der Waals attraction increases over time, and the rate of increase is related to the rate of particle deformation due to greater contact area. Furthermore, these forces increase as the particle size increases. See, for example, FIG. 1, which is a graphical representation of mathematical calculations of the foregoing forces.

The above-described problems are addressed, among others, by the current invention. In one aspect, the present invention provides for inhalers with modified substrates which alter the attractive forces. Preferably, greater than about 70%, and preferably greater than about 80% of the medicament is released upon inhalation. Preferably, the air flow required for release of about 80% to about 100% of the medicament in a dosage unit is less than about 60 liters per minute; more preferably, less than about 30 liters per minute, and even more preferably, no greater than about 15 liters per minute. See, for example, FIGS. 2A–E which show release of a medicament from a textured substrate having grooved indentations at 15 liters per minute (B), 30 liters per minute (C), 45 liters per minute (D), and 57 liters per minute (E). See also FIG. 2F which is a graph of the data obtained and which shows the increasing release of medicament from the substrate as air flow increases. Example 1 provides the data used to generate the graph shown in FIG. 2F. The deposition technique used in this example involved ion printing according to Ser. No. 08/471,889. In preferred embodiments of the present invention, an electrostatic chuck is used to deposit electrostatically charged medicament onto the inhaler substrate, as described, for example, in U.S. Ser. No. 08/630,050. A preferred deposition technique, using an electrostatic chuck, is believed to result in a higher percentage of release of the medicament from the inhaler substrate. Other deposition techniques can also be used with the modified inhaler substrates of the invention.

The inhaler substrate is preferably modified to minimize the surface area of the contact between the particles of the powder and the surface of the substrate, for those particles having a selected size. Particles having the desired size will have minimal contact with the substrate, and will therefore be more likely to be released from the substrate. In addition to making it more likely to release the desired particles, the modified substrate can be configured so that particles having an undesirable size are trapped. For example, if the surface area of contact between the particle and the substrate is high, such as with a particle having a size below the selected size, the higher contact leads to trapping the particle on the substrate rather than releasing it.

The minimization of the area of contact is preferably accomplished in the following ways. The surface area of contact can be minimized, for example, by providing indentations in the plane of the surface, or by providing raised areas in the plane of the surface. In preferred embodiments of the invention at least one interior surface of the inhaler has indentations or raised areas with valleys therebetween, or other surface modification for decreasing the area of contact between the selected medicament particles and the interior surface of the inhaler in contact with the medicament. The contact of the medicament with the surface can occur, for example, before inhalation or during inhalation, such as contact with the substrate during deposition before inhalation, or contact with an interior surface of the mouthpiece during inhalation. Preferably, both the surface of the substrate upon which medicament is deposited and the mouthpiece and any other surfaces having contact with the medicament have indentations or raised areas therein, or any other surface structure for decreasing the area of contact between the selected medicament and the surface.

The indentation or raised area may be, for example, linear, tortuous, curved, circular, or any other desired configuration. In certain preferred embodiments the indentations are in the form of linear grooves, which provides, for example, for ease of manufacturing. See, for example, FIGS. 3A–C, which show release from a polypropylene substrate having grooved indentations.

Specifically, FIG. 3A is a micrograph of the substrate, which has grooved indentations therein, prior to deposition. FIG. 3B is a micrograph of the substrate of FIG. 3A after deposition of the medicament powder thereon. FIG. 3C is a micrograph of FIG. 3B after release of the medicament from the substrate. See, also, for example, FIGS. 4–6 which show three increasing magnifications of release from silicon. FIG. 4 has the lowest magnification, FIG. 5 has an intermediate magnification, and FIG. 6 has the highest magnification. A 100 micron bar is provided in FIGS. 4 and 5 for size reference, and a 10 micron bar is provided in FIG. 6 for size reference. Part A of each of these figures is a photomicrograph of the substrate before deposition. Part B of each of these figures is a photomicrograph of the substrate after deposition of the medicament powder. Part C of each figures is a photomicrograph of the substrate after release of the powder.

Preferably, the depth of an indentation or the height of a raised area is slightly smaller than the size of the smallest particle desired to released from the inhaler, such as about 5% to about 50% smaller, and more preferably, about 5% to about 20% smaller than the smallest selected particle.

The width of the indentation or the valley between two raised areas is preferably slightly smaller than the diameter of the smallest particle selected to be released, such as about 5% to about 20% smaller, and more preferably, about 10% to about 20% smaller. For example, if the particles to be released from the inhaler have a selected size of about 2 to about 6 microns, the width of the indentation or valley will preferably be about 1.8 microns. Preferably, the diameter of the indentation or valley is less than the diameter of the minimum respirable medicament particle size. For example, the pitch of the substrate, measured from the center of a valley to the center of a raised area, is preferably about 1 to about 2.5 microns for dispensing particles from about 2 to about 6 microns. Particle size can be determined, for example, using scanning electron microscopy.

In addition to indentations and raised areas, the surface area of the contact between the medicament and the substrate may be decreased, for example, by using a perforated substrate. Furthermore, more than one such modification may be made to a single substrate. Preferably, the entire surface area of the surface in contact with the powder particles is modified to have minimized contact with the medicament powder.

A further aspect of the present invention is the use of a selected material to form the surface of the substrate in contact with the powder particles. Preferably, the material is selected in part on the basis of low surface energy. See, for example, Kaelble, *Physical Chemistry of Adhesion* at pages 149–164 (John Wiley & Sons 1971), which is hereby incorporated by reference herein in its entirety. Preferably, the surface energy of the surface in contact with the powder particles is between about 10 to about 25 dynes/cm. More preferably, the surfaces, when uncharged, have no substantial van der Waals or electrostatic interaction with the medicament. Furthermore, the material is preferably substantially chemically unreactive with the medicament. Examples of materials that can be used for such surfaces include perfluorinated polymers such as polytetrafluoroethylene ("TEFLON"), silicone, silicon alumina ceramic, polymeric photoconductor, polycarbonate, polyimide, polypropylene and polyethylene. In some embodiments, the surface has reacted with a silane, such as fluorosilane or aminosilane, to form a film having a low surface energy. Alternatively, for example, the surface can be treated to apply a perfluorinated polymer film. See, for example, U.S. Pat. No. 4,252,848, which is incorporated by reference herein in its entirety. See also, for example, the chapter entitled "The Properties of Fluorocarbon Films Prepared by Plasma Polymerization of 1,3-Perfluorodimethylcyclohexane" in S. Peprek and J. Hertz, eds., *4th International Symposium on Plasma Chemistry* (vol. 1 1979) at pages 152–163, which is hereby incorporated by reference herein in its entirety.

The material forming the surface in contact with the powder particles is also preferably selected on the basis of low chemical reactivity with the powder particles. For example, if the powder to be deposited upon the substrate is a charged or polar particle, the surface of the substrate is preferably not charged or polar. The materials used to form the surfaces in contact with the medicament are preferably selected to minimize the van der Waals and electrostatic adhesion of the medicament, as well as to minimize chemical reactivity.

Further, the material used to form the surface in contact with the medicament is preferably hard, and not pliable, particularly since pliability tends to increase contact area. See, for example, Nielsen, *Mechanical Properties of Polymers and Composites* (Marcel Dekker Inc., NY 1974) at pages 367–369, which is hereby incorporated by reference herein in its entirety. Preferably, the material has a Vickers hardness greater than about 10 kp/mm$^2$, such as polystyrene, polymethyl methacrylate, polycarbonate, polyacetal, polyethylene terephthalate and phenolic resin.

Preferably, the material used to make a surface in contact with the medicament is a polymer. Preferred materials for use in such surfaces include polytetrafluoroethylene, silicon, alumina ceramic, aluminized organic photoconductor, polyvinyl carbazole, polycarbonate, polyimide and polyethylene. In certain embodiments, the indentations are the grooves present in an alumina ceramic printed board. See, for example, FIGS. 4–6. In one embodiment, a die stamp having 2 micron spaced grooves is used to emboss a substrate, thereby creating a substrate with the desired indentations therein. See, for example, FIG. 3.

In certain preferred embodiments, the surface is treated with a silane, such as fluorosilane or aminosilane. In some embodiments, polyimide is not preferred since in some instances, it may adhere a powder due to a chemical or electrostatic interaction. Preferably, the materials used and the surface treatment, if any, are pharmaceutically acceptable and do not cause substantial toxicity.

The size and shape of the substrate can be selected based upon the application. In some instances, for example, the substrate will be in the form of a disk or elongated such as a tape. Preferably, multiple dosage units are deposited onto the substrate, each dosage unit being in a discrete area, separated by an area of the substrate having no powder deposited thereon. In preferred embodiments, the substrate is sealed for protection, such as against the environment, including humidity, as well as for sterility The advantages of the inhaler apparatus of the present invention include its operation in releasing powder without the use of mechanical force, such as a hammer. The requirement of mechanical force to release the powder may mean that the powder is unintentionally released, for example, upon dropping the inhaler.

Although the inhalers of the present invention are designed for release of the medicament powder upon inhalation, preferably they do not release the medicament prior to inhalation. Preferably, for example, the medicament will remain on the substrate after the inhaler apparatus is subjected to a drop test, such as dropping the inhaler into a tube from a height of about 48 inches at a temperature of about 65 degrees Celsius and a relative humidity of about 65%.

In preferred aspects of the present invention, the inhaler apparatus further includes a mouthpiece with a configuration that prevents adherence of the medicament powder For example, the mouthpiece preferably has an interior surface that is selected to resist adhering the powder particles. For example, the interior surface preferably has indentations or raised areas thereon, such as the modifications described above, to promote release of the powder. Preferably, the surface area of the interior surface of the mouthpiece is increased by using indentations in the form of grooves that are parallel to the direction of air flow in the mouthpiece, preferably causing substantially laminar air flow.

Figure 7:
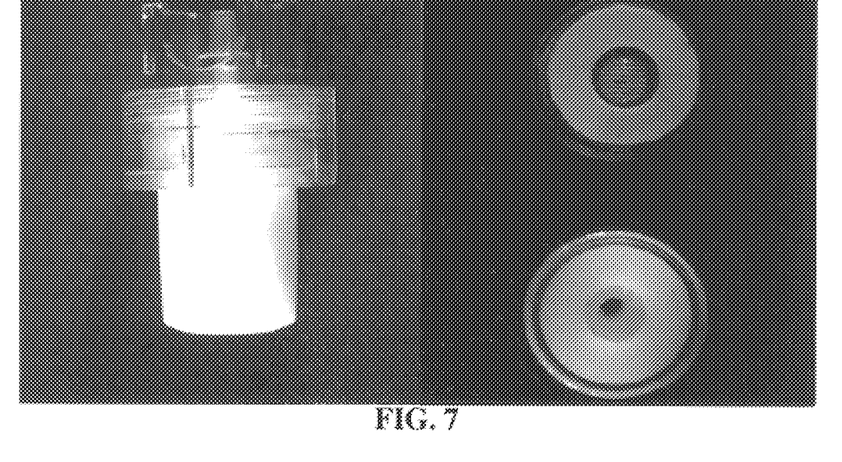
Figure 8A:
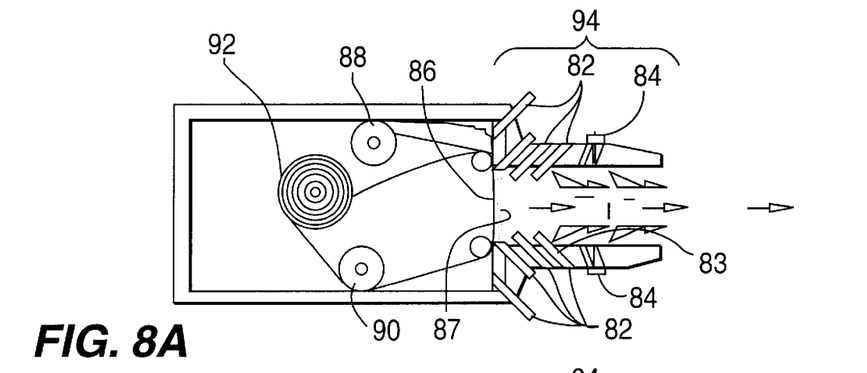
Figure 8B:
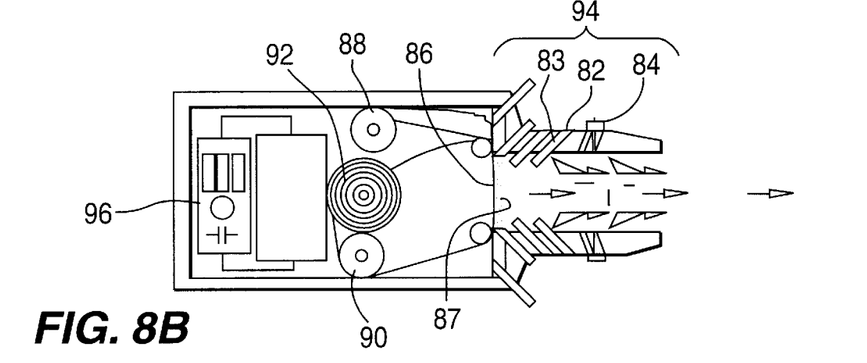

In additional preferred aspects of the present invention, the mouthpiece has multiple air inlets with a channel connected to each inlet for the enhancement of release of medicament powder. See, for example, FIG. 7, in which the arrows point to the inlets. The channel connects the interior of the mouthpiece to the ambient atmosphere through an opening termed an "air inlet hole." Preferably, the air inlet hole is created, such as drilled, at an angle, preferably about 20 to about 70 degrees, and more preferably, about 45 degrees. Preferably, each channel extends from the corresponding air inlet at an angle of about 20 degrees to about 70 degrees. More preferably, the channel forms an angle of about 45 degrees from the horizon. In preferred embodiments, the channels are cylindrical and have a diameter of less than about 5 mm, such as about 0.1 to about 5 mm. Preferably, the mouthpiece is configured to maximize air flow between the powder and the substrate so that the powder is readily released from the substrate upon inhalation. In certain preferred embodiments, there are about 2 to about 20 air inlets and corresponding channels, and in other preferred embodiments, there are about 4 to about 8 air inlets.

Preferably, the air inlets can be opened and closed at will by the patient, or automatically via a shuttering mechanism, to maintain a constant pressure drop regardless of the air flow.

Illustrations of embodiments of the inhaler apparatus of the invention having multiple air inlets with channels connected to each inlet are provided in FIGS. 8A and 8B. FIG. 8A shows a mouthpiece 94 with air inlets 82 having channels 83 attached thereto. A shuttering mechanism 84 is provided for several of the air inlets. The mouthpiece 94 is in air flow communication with the substrate 86 having medicant 87 deposited thereon. The substrate 86 is in the form of an elongated tape, which is provided by reel 92 and taken up by reel 90. The substrate has a seal (not shown) which is taken up by reel 88. FIG. 8B illustrates the inhaler of FIG. 8A, further including an electronic release mechanism (not shown) powered by a battery 96.

In certain embodiments, each air inlet is connected via the channel to a portion of an individual dosage. For example, a dosage of 100 micrograms can be administered by aligning each of four 25-microgram dosages with each of four air inlets.

Preferably, only particles of the desired size, such as the respirable fraction, are deposited onto the substrate of the inhaler. Since the apparatus is preferably used with the medicament deposited in the desired particle range, and since in preferred embodiments, a substantial amount of undesired particle size range may be trapped on the substrate, there may be no need for additional devices to promote deagglomeration. Thus, the present invention provides advantages over inhalers requiring devices to deagglomerate, such as tortuous channels, that can trap medicament. In certain pharmaceutical applications, preferably the size of the particles dispensed by the inhaler is no greater than about 15 microns, and more preferably, no greater than about 10 microns.

In preferred embodiments, the substrate of the inhaler is equipped with a conductive layer for electronic assistance of release of the powder, as described in co-pending application entitled “Inhaler Apparatus with an Electronic Means for Enhanced Release of Dry Powders”, filed simultaneously herewith.

The inhaler can also be equipped with other mechanisms for enhancing release, including an electron emitter such as a diamond tip emitter or other electron emitter, in order to neutralize the charge holding the powder onto the substrate. Alternatively, for example, the substrate upon which the medicament is deposited may be a photoconductive substrate that releases the medicament upon the application of light.

It will be understood by those skilled in the art that the inhalers of the invention can be used with numerous types of medicaments, and in addition to oral administration, the inhalers of the invention can be used with nasal administration.

The present invention is further illustrated by the following non-limiting examples.

EXAMPLE 1

Release of Powdered Medicament from Modified Substrate

Figure 3A:
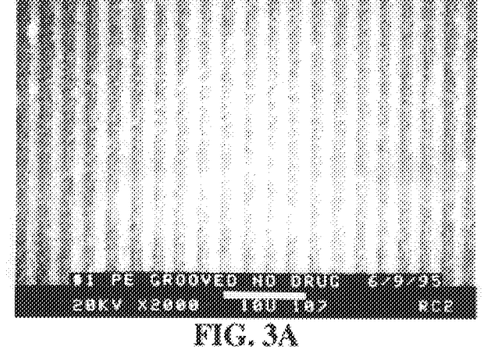
Figure 3B:
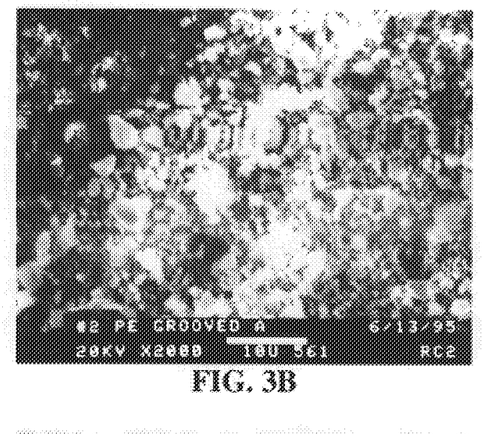
Figure 3C:
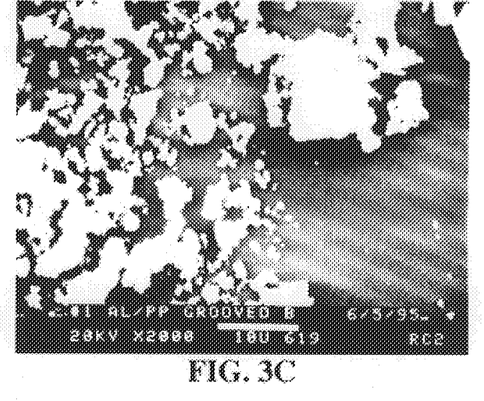
Figure 4A:
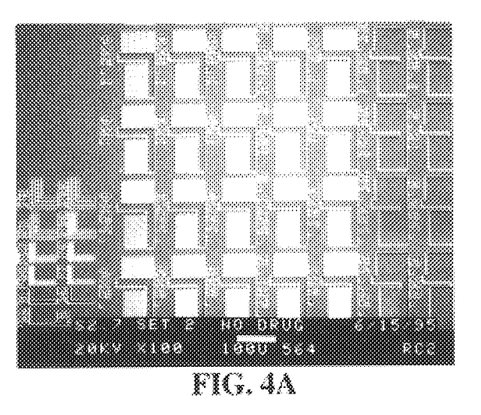
Figure 4B:
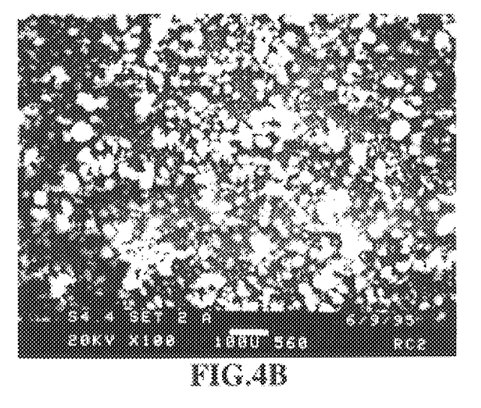
Figure 4C:
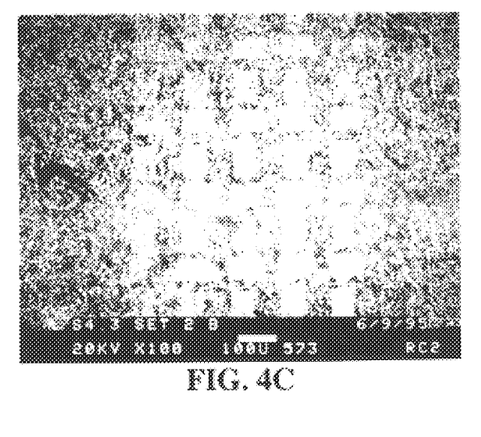
Figure 5A:
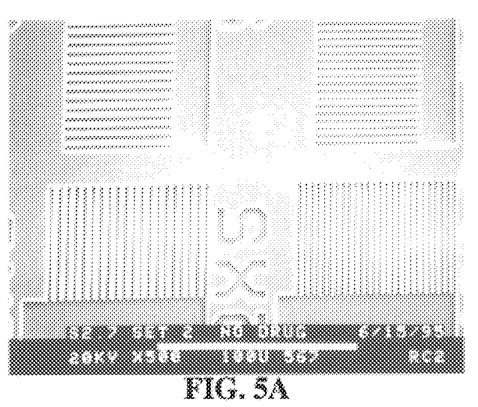
Figure 5B:
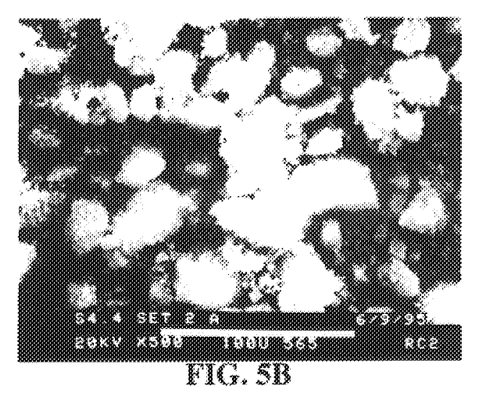
Figure 5C:
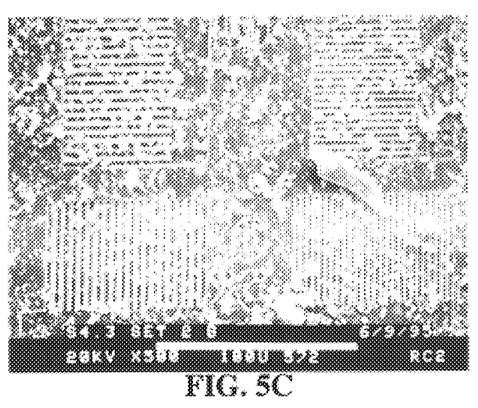
Figure 6A:
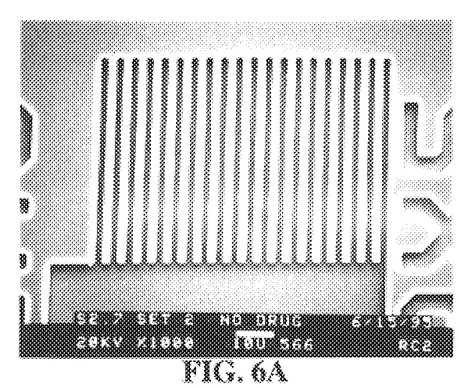
Figure 6B:
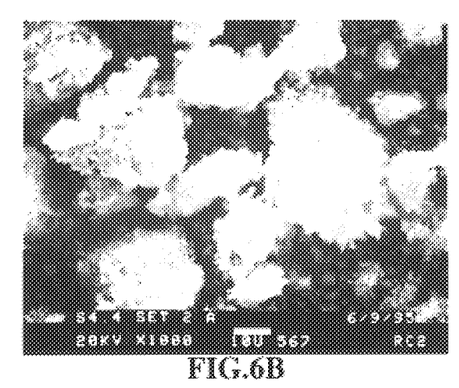
Figure 6C:
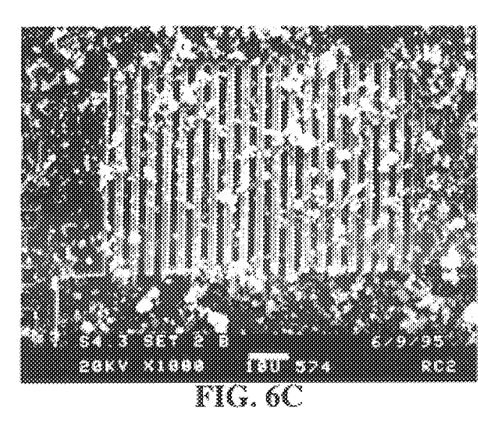

A modified polypropylene substrate, as shown in FIG. 3 was tested for release of a powdered medicament, mometasone furoate. A 2 $cm^2$ square of substrate was first weighed in milligrams on a microbalance ("sub(mg)"). Then, powdered medicament was deposited on the substrate, using the ion printing technique disclosed in U.S. Ser. No. 08/471,889. The medicament was deposited in four dots, using several bursts of air to dispense a powder cloud. Next, the substrate was weighed with the medicament thereon ("sub+drug," which is provided in mg). The weight of the medicament ("drug(mg)") was determined by substracting the weight of the substrate before deposition ("sub(mg)") from the weight of the substrate after deposition ("sub+drug"). Two weight measurements were taken for each data point, and the two weight measurements were averaged ("average").

Figure 1:
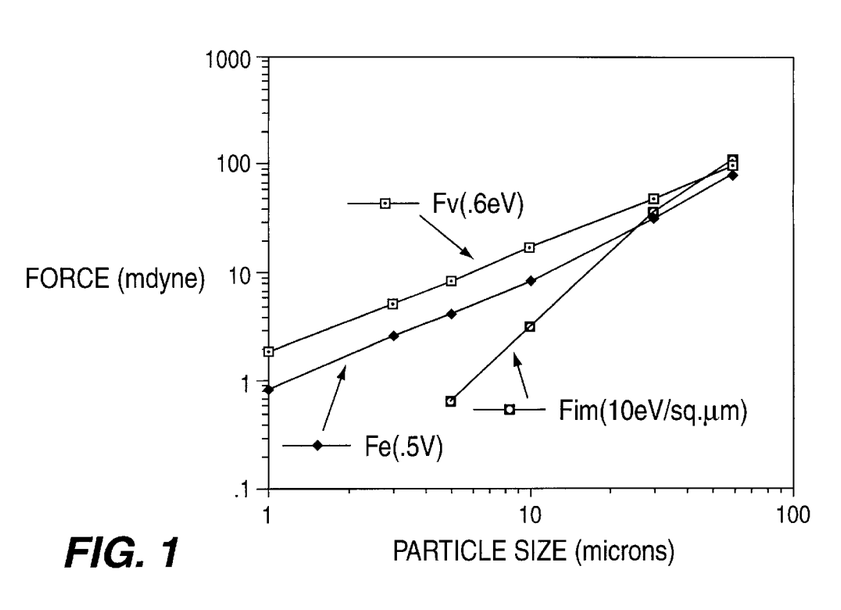
FIG. 1 is a graphical representation of 3 forces that adhere particles to the substrate of the inhaler; electrostatic forces ("Fe"), charge imaging forces ("Fim") and van der Waals forces ("Fv").
Figure 2A:
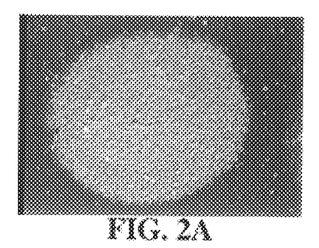
Figure 2B:
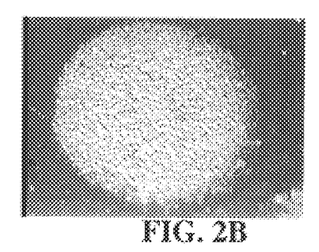
Figure 2C:
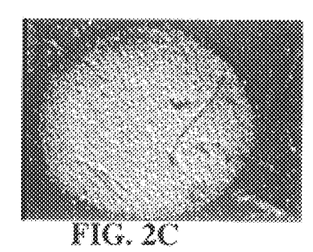
Figure 2D:
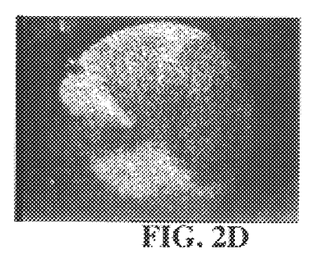
Figure 2E:
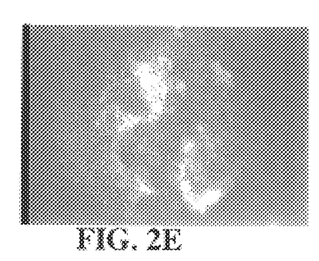
Figure 2F:
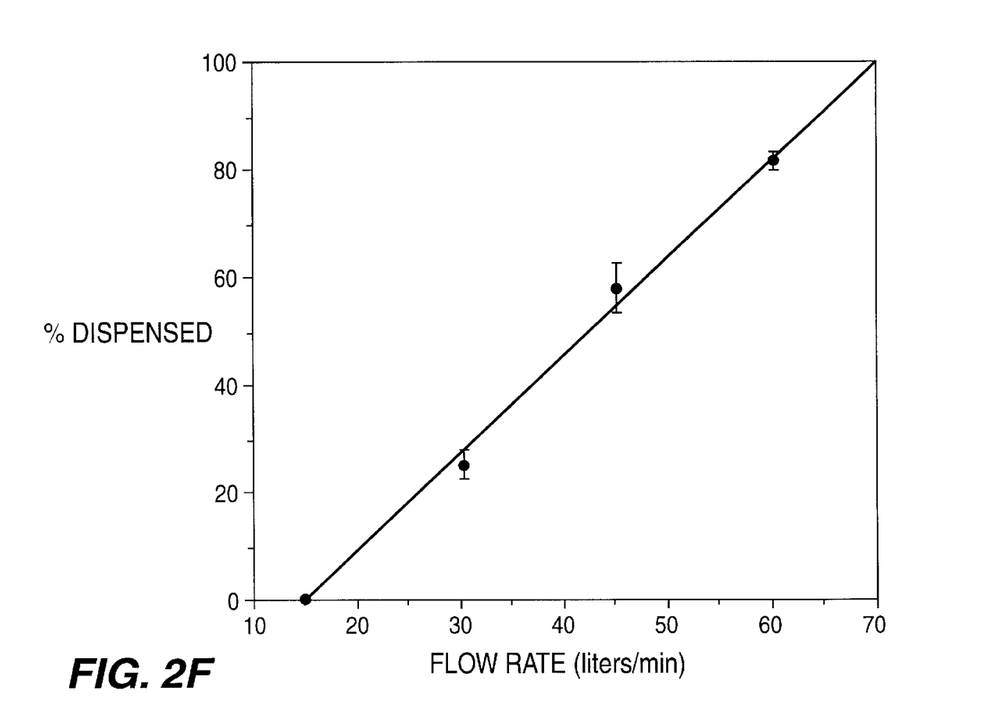
Figure 9:
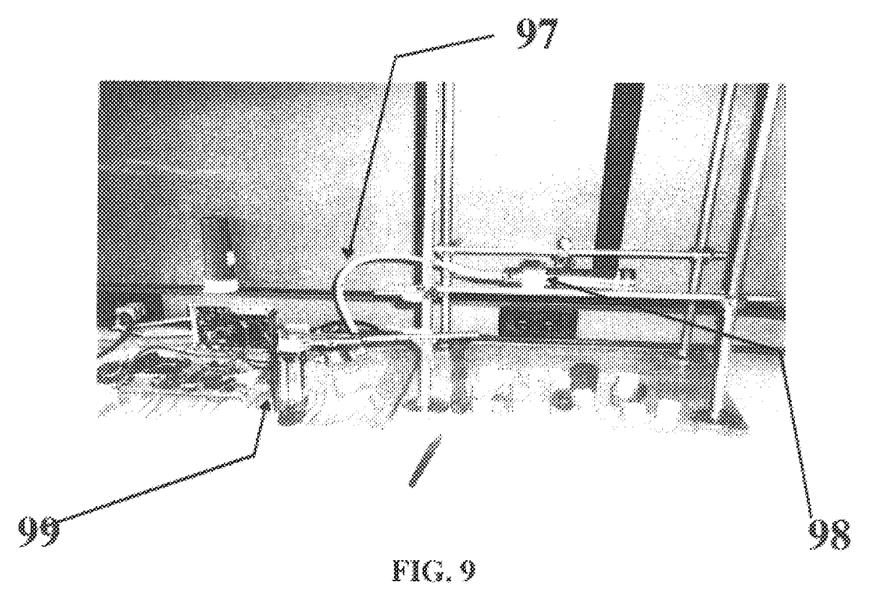
Figure 10:
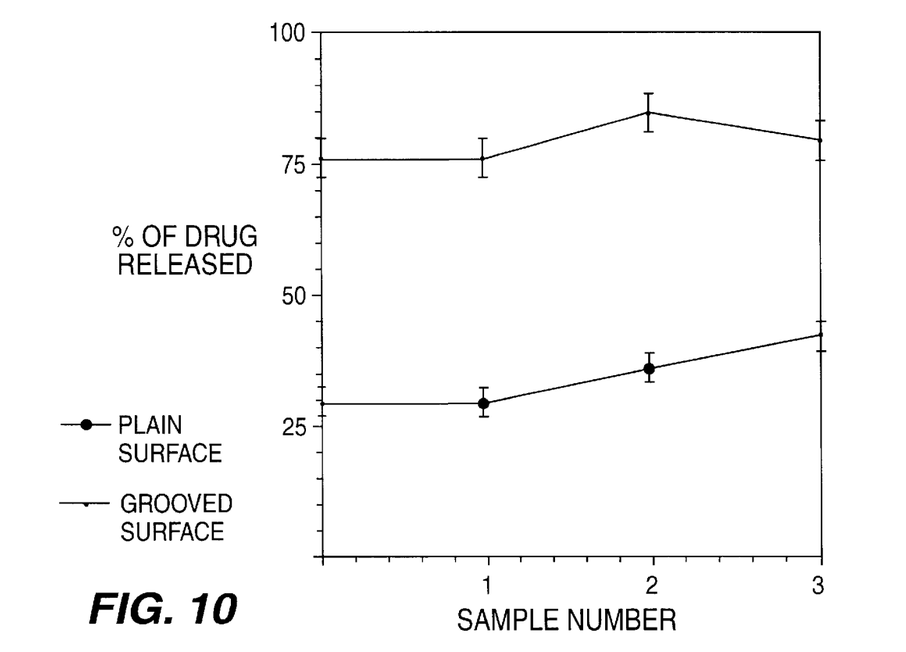

To dispense the powder, the substrate was placed in an apparatus such as that shown in FIG. 9, and an inhaler mouthpiece was attached to the cylinder 98. The inhaler mouthpiece included 8 air inlets, each having a channel (capillary tubes) at a 45 degree angle from the mouthpiece to enhance lift off of the medicament powder. The release of the powder from the substrate was tested at four different flow rates of air applied to the substrate through the mouthpiece; 15, 30, 45 and 57 liters per minute. "Flow rate" indicates the air flow rate used to release the medicament from the inhaler. The substrate was weighed after release of the drug ("sub-drug," which is indicated in mg). The percentage of drug released from the substrate ("%drug") was determined using the weight of the drug left after release and the weight of the drug before release. "Humid./temp" indicates the percentage of humidity and ambient temperature (degrees Farenheit) at the time of the testing. The results are shown in Tables 1–2 below Table 3 summarizes the data in Tables 1–2 by providing the average percentage of medicament release for each of the three flow rates, and the standard deviations. The data in Table 3 is depicted graphically in FIG. 2F.

TABLE 1

| Sample | # appl/psi | sub + drug (mg) | sub (mg) substrate | drug(mg) (mg) | sub-drug after dispensing | Drug left (mg) | % drug dispensed | flow rate (liters/min) | humid./ temp./ |
|---|---|---|---|---|---|---|---|---|---|
| 1 | 5/7.5 | 8.7735 | 8.6095 | | 8.6494 | | | 57 | 68/81 |
| | | 8.7735 | 8.6092 | | 8.6495 | | | | |
| average | | 8.7735 | 8.60935 | 0.16415 | 8.64945 | 0.0401 | 75.57112 | | |
| 2 | 5/7.5 | 7.2482 | 7.1406 | | | | | 57 | 67/81 |
| | | 7.2486 | 7.1409 | | | | | | |
| average | | 7.2484 | 7.14075 | 0.10765 | 7.16 | 0.01925 | 82.11797 | | |
| | | | | | 8.2274 | | | | |
| 3 | 4/7.5 | 8.3174 | 8.1912 | | 8.2257 | | | n/d | 68/81 |
| | | 8.3161 | 8.1911 | | 8.2238 | | | | |
| average | | 8.31675 | 8.19115 | 0.1256 | 8.225633333 | 0.0344833 | 72.54512 | | |
| 4 | 4/7.5 | 6.8848 | 6.7813 | | | | | n/d | 68/81 |
| | | 6.8844 | 6.7816 | | | | | | |
| average | | 6.8846 | 6.78145 | 0.10315 | n/d | | | | |
| 5 | 5/7.5 | 8.7858 | 8.681 | | | | | 45 | 68/81 |
| | | 8.7862 | 8.682 | | | | | | |
| average | | 8.786 | 8.6815 | 0.1045 | 8.7215 | 0.04 | 61.72249 | | |
| 6 | 3/7.5 | 7.6297 | 7.5486 | | 7.5782 | | | n/d | 68/90 |
| | | 7.63 | 7.547 | | 7.582 | | | | |
| average | | 7.62985 | 7.5478 | 0.08205 | 7.578133333 | 0.0303333 | 83.03067 | | |
| 7 | 4/7.5 | 8.1118 | 7.9899 | | | | | 15 | 68/90 |
| | | 8.1117 | 7.9905 | | | | | | |
| average | | 8.11175 | 7.9902 | 0.12155 | | | 6.3 | | |
| 8 | 5/7.5 | 7.517 | 7.4066 | | | | | 30 | 68/90 |
| | | 7.5168 | 7.4063 | | | | | | |
| average | | 7.5169 | 7.40645 | 0.11045 | 7.4913 | 0.08485 | 23.17791 | | |

TABLE 2

| Sample | # appl/psi | sub (mg) (samp + subs) | sub + drug substrate | drug(mg) (mg) | sub-drug after dispensing | Drug left (mg) | % drug dispensed | flow rate (liters/min) | humid./temp temp (F)t |
|---|---|---|---|---|---|---|---|---|---|
| 9 | 6/7.5 | 7.0404 | 6.9084 | | 6.9337 | | | 60 | 67/83 |
| | | 7.0408 | 6.9086 | | 6.9344 | | | | |
| average | | 7.0406 | 6.9085 | 0.1321 | 6.93405 | 0.02555 | 80.658592 | | |
| 10 | 4/7.5 | 7.5945 | 7.4758 | | 7.5067 | | | 45 | 66/83 |
| | | 7.5938 | 7.4765 | | 7.507 | | | | |
| average | | 7.59415 | 7.47615 | 0.118 | 7.50685 | 0.0307 | 73.983051 | | |
| 11 | 3/7.5 | 8.037 | 7.9513 | | 8.037 | | | 15 | 66/83 |
| | | 8.0371 | 7.9514 | | 8.0366 | | | | |
| average | | 8.03705 | 7.95135 | 0.0857 | 8.0368 | 0.08545 | 0.2917153 | | |
| 12 | 4/7.5 | 8.8213 | 8.7376 | | 8.8202 | | | 15 | 65/83 |

TABLE 2-continued

| Sample | # appl/psi | sub (mg) (samp + subs) | sub + drug substrate | drug(mg) | sub-drug after dispensing | Drug left (mg) | % drug dispensed | flow rate (liters/min) | humid./temp temp (F)t |
|---|---|---|---|---|---|---|---|---|---|
| | | 8.8207 | 8.7375 | | 8.8212 | | | | |
| average | | 8.821 | 8.73755 | 0.08345 | 8.8207 | 0.08315 | 0.3594967 | | |
| 13 | 5/7.5 | 7.1802 | 7.1081 | | 7.1794 | | | 15 | 65/83 |
| | | 7.1796 | 7.1081 | | 7.1795 | | | | |
| average | | 7.1799 | 7.1081 | 0.0718 | 7.17945 | 0.07135 | 0.6267409 | | |
| 14 | 3/7.5 | 6.8602 | 6.7494 | | 6.8293 | | | 30 | 70/84 |
| | | 6.8597 | 6.7485 | | 6.8294 | | | | |
| average | | 6.85995 | 6.74895 | 0.111 | 6.82935 | 0.0804 | 27.567568 | | |
| 15 | 5/7.5 | 9.3052 | 9.1824 | | 9.2381 | | | 45 | 70/86 |
| | | 9.305 | 9.1825 | | 9.238 | | | | |
| average | | 9.3051 | 9.18245 | 0.12265 | 9.23805 | 0.0556 | 54.667754 | | |
| 16 | 5/7.5 | 8.983 | 8.8723 | | 8.9582 | | | 30 | 71/86 |
| | | 8.9845 | 8.8727 | | 8.958 | | | | |
| average | | 8.98375 | 8.8725 | 0.11125 | 8.9581 | 0.0856 | 23.05618 | | |
| 17 | 7/7.8 | 9.3624 | 9.2077 | | 9.2326 | | | 60 | 70/86 |
| | | 9.3623 | 9.2081 | | 9.2324 | | | | |
| average | | 9.36235 | 9.2079 | 0.15445 | 9.2325 | 0.0246 | 84.072515 | | |

TABLE 3

| flow rate | 57 | 45 | 30 | 15 |
|---|---|---|---|---|
| | 80.658592 | 54.6677538 | 27.5675676 | 0.29171529 |
| | 84.0725154 | 73.9830508 | 23.0561798 | 0.3594967 |
| | 82.1179749 | 61.722488 | 23.1779086 | 0.62674095 |
| average | 82.28302743 | 63.4577642 | 242.600552 | 0.425984313 |
| standard deviation | 1.712936076 | 9.773871401 | 2.570231634 | 0.177132719 |
| w/ one data point dropped | 80.658592 | 54.6677538 | 27.5675676 | 0.29171529 |
| | 84.0725154 | | 23.0561798 | 0.3594967 |
| | 82.1179749 | 61.722488 | 23.1779086 | 0.62674095 |
| average | 82.28302743 | 58.1951209 | 24.600552 | 0.425984313 |
| standard deviation | 1.712936076 | 4.988450392 | 2.570231634 | 0.177132719 |

EXAMPLE 2

Comparison of Modified Substrate to Unmodified Substrate

Approximately 50 μg dots of inhalation medicament were deposited on a 2 cm² polypropylene substrate using the ion printing process described in Ser. No. 08/471,889 ("Methods and Apparatus for Electrostatically Depositing a Medicament Powder Upon Predefined Regions of a Substrate," filed Jun. 6, 1995). The weight of the medicament was verified using a microbalance.

The release of medicament from an inhaler substrate having medicament deposited thereon was tested using the apparatus shown in FIG. 9. Referring to FIG. 9, air flow was generated through the use of a vacuum (not shown) attached to tubing 97, which was in turn attached to a cylinder 98, for attachment to an inhaler mouthpiece (not shown). The mouthpiece including 8 air inlets, each having a channel (capillary tubes) at 45 degree angles to the mouthpiece. A flow meter 99 was used to measure the rate of air flow. Three samples of each of two different substrates were tested, the first substrate having a grooved surface, as shown in FIG. 3, and the second substrate having an unmodified planar surface. Both substrates were made of polypropylene. The results of the testing are shown in Table 4 below.

TABLE 4

| Sample number | % medicament released from grooved substrate | % medicament released from planar substrate |
|---|---|---|
| 1 | 80.5 | 62 |
| 2 | 84 | 64.5 |
| 3 | 82 | 67 |
| Average Value | 82.16 | 64.5 |
| Standard Deviation | 1.84 | 2.5 |

The data shown above is depicted graphically in FIG. 10, which shows that release of the medicament from the substrate with indentations in the form of grooves was much higher than the release from an unmodified substrate.

We claim:

1. An inhaler apparatus comprising interior surfaces having contact with medicament particles of a selected size range for inhalation, the interior surfaces including an interior surface of a mouthpiece and a substrate with medicament particles deposited thereon, at least one of such interior surfaces being a textured surface comprising indentations or raised areas defining valleys of dimensions and spacings selected to decrease the area of contact between medicament particles of a selected size range and the textured surface, thereby reducing the adherence of the medicament particles to the textured surface.

2. The inhaler apparatus of claim 1, wherein the textured surface has medicament particles deposited thereon.

3. The inhaler apparatus of claim 1, wherein the textured surface is an interior surface of the mouthpiece of the inhaler.

4. The inhaler apparatus of claim 1, wherein the valleys have widths that are about 5% to about 20% smaller than a minimum selected particle size to be administered by the inhaler.

5. The inhaler apparatus of claim 1, wherein the valleys have a width of about 1 micron to about 2.5 microns.

6. The inhaler apparatus of claim 1, wherein the valleys have a depth that is about 5% to about 50% smaller than a minimum selected particle size to be administered by the inhaler.

7. The inhaler apparatus of claim 1, wherein the valleys are substantially regularly spaced throughout the area of the substrate having medicament particles thereon or throughout the mouthpiece of the inhaler.

8. The inhaler apparatus of claim 1, wherein the valleys are substantially linear.

9. The inhaler apparatus of claim 1, wherein the substrate comprises a disk or a tape.

10. The inhaler apparatus of claim 1, wherein the substrate comprises multiple dosage units of medicament particles.

11. The inhaler apparatus of claim 1, further comprising a seal for sealing the substrate with medicament particles thereon.

12. The inhaler apparatus of claim 1, wherein the textured surface is made of a material having a low surface energy.

13. The inhaler apparatus of claim 1, wherein the textured surface is made of a material that is substantially chemically unreactive with the medicament particles.

14. The inhaler apparatus of claim 12, wherein the textured surface is made of a material selected from the group consisting of polytetrafluoroethylene, silicon, alumina ceramic, aluminized organic photoconductor, polycarbonate, polyimide, polypropylene and polyethylene.

15. The inhaler apparatus of claim 1, wherein the textured surface has a layer of a silane thereon.

16. The inhaler apparatus of claim 15, wherein the silane is fluorosilane or aminosilane.

17. The inhaler apparatus of claim 1, wherein substantially all interior surfaces of the inhaler apparatus that have deposited medicament particles or which contact medicament particles during use have textured surfaces.

18. The inhaler apparatus of claim 1 wherein the dimensions and spacings of the valleys of the textured surface are selected to reduce the area of the medicament particles of a selected size range contacting the textured surface.

19. The inhaler apparatus of claim 5, wherein the pitch of the valleys is from about 1 micron to about 2.5 microns.

20. An inhaler apparatus comprising a mouthpiece, the mouthpiece having a wall with an exterior surface and a textured interior surface comprising indentations or raised areas defining valleys of dimensions and spacings selected to decrease the area of contact between medicament particles of a selected size range and the textured surface, thereby reducing the adherence of medicament particles to the textured surface, the mouthpiece further comprising multiple air inlets extending from the exterior to the interior, the inlets each being in communication with a channel, each channel extending from the interior to the exterior of the mouthpiece, and each channel being positioned at an angle of about 20 to about 70 degrees from the wall of the mouthpiece.

21. The inhaler apparatus of claim 20, wherein the channels are positioned at an angle of about 45 degrees from the wall of the mouthpiece.

22. The inhaler apparatus of claim 20, wherein the channels are substantially cylindrical in shape.

23. The inhaler apparatus of claim 20, wherein the channels are less than about 5 mm in diameter.

24. The inhaler apparatus of claim 20, wherein the valleys are substantially parallel to the direction of air flow in the mouthpiece during inhalation.

25. The inhaler apparatus of claim 20, wherein the valleys have widths that are about 5% to about 20% smaller than the minimum particle size to be administered by the inhaler.

26. The inhaler apparatus of claim 20, wherein the indentations or valleys have a depth that is about 5% to about 50% smaller than a minimum selected particle size to be administered by the inhaler.

27. The inhaler apparatus of claim 17, further comprising a shuttering mechanism for selectively closing at least one of the air inlets to control a pressure differential between the exterior and interior of the inhaler apparatus.

28. A method of manufacturing an inhaler apparatus, comprising:

(a) providing a substrate having a surface for deposition of medicament particles, the substrate surface being a textured surface comprising indentations or raised areas defining valleys of dimensions and spacings selected to reduce the area of contact between particles that of a selected size range and the textured surface, (b) depositing medicament particles on the substrate; and (c) incorporating the substrate into a housing, the housing having a mouth piece for inhalation.

29. The method of claim 28, wherein the deposition is performed electrostatically.

30. The method of claim 28, further comprising sealing the substrate having medicament particles deposited thereon.

31. The method of claim 28, wherein the medicament particles deposited on the substrate has a particle size of about one to about fifteen microns.

* * * * *